(12) United States Patent
Rasmussen (10) Patent No.: US 9,724,220 B2
(45) Date of Patent: Aug. 8, 2017

(54) INTRODUCER ASSEMBLY AND IMPLANTABLE MEDICAL DEVICE

(75) Inventor: Erik Edelboe Rasmussen, Slagelse (DK)

(73) Assignee: Cook Medical Technologies LLC, Bloomington, IN (US)

( * ) Notice: Subject to any disclaimer, the term of this patent is extended or adjusted under 35 U.S.C. 154(b) by 130 days.

(21) Appl. No.: 12/755,880

(22) Filed: Apr. 7, 2010

(65) Prior Publication Data

US 2010/0256725 A1    Oct. 7, 2010

(30) Foreign Application Priority Data

Apr. 7, 2009 (GB) .................................. 0906062.5

(51) Int. Cl.
*A61F 2/962* (2013.01)
*A61F 2/07* (2013.01)
(Continued)

(52) U.S. Cl.
CPC ............... *A61F 2/962* (2013.01); *A61F 2/07* (2013.01); *A61F 2/89* (2013.01); *A61F 2002/075* (2013.01); *A61F 2002/8483* (2013.01); *A61F 2002/9517* (2013.01); *A61F 2220/0016* (2013.01)

(58) Field of Classification Search
None
See application file for complete search history.

(56) References Cited

U.S. PATENT DOCUMENTS

| 5,755,777 A | 5/1998 | Chuter |
|---|---|---|
| 5,855,601 A | 1/1999 | Bessler et al. |

(Continued)

FOREIGN PATENT DOCUMENTS

| EP | 1506747 A2 | 2/2005 |
|---|---|---|
| EP | 1935376 A2 | 6/2008 |

(Continued)

OTHER PUBLICATIONS

European Patent Office Examination Report for corresponding EP Appln. No. 10 714 405.7 dated Oct. 3, 2013 (5 pages).

(Continued)

*Primary Examiner* — Thomas J Sweet
*Assistant Examiner* — Megan Wolf
(74) *Attorney, Agent, or Firm* — Brinks Gilson & Lione (57) ABSTRACT

An introducer for deploying an implantable medical device such as a stent (60), stent graft (80) or other similar device is provided with an outer sheath (132,232) which is provided with a series of internally longitudinally extending channels (136. 236) and interdigitating protrusions (134, 234) extending therein. At least on stent ring (0) of the medical device is provided with one or more barbs (104) which point radially outwardly of the device, including when this is compressed onto the introducer. The barbs (104) lie within the channels (136, 236) which the remainder of the medical device is retained in its compressed form by the elongate protrusions (134, 234). The channels (136, 236) allow for the provision of relatively stiff barbs (104). The barbs (104) can be better suited to ensuring the correct placement of the medical device than flexible barb arrangements.

8 Claims, 4 Drawing Sheets

(51) Int. Cl.
  *A61F 2/848* (2013.01)
  *A61F 2/95* (2013.01)
  *A61F 2/89* (2013.01)

(56) References Cited

U.S. PATENT DOCUMENTS

| | | | |
|---|---|---|---|
| 6,355,060 | B1 | 3/2002 | Lenker et al. |
| 6,451,051 | B2 | 9/2002 | Drasler et al. |
| 6,517,573 | B1* | 2/2003 | Pollock ............... A61F 2/07 623/1.13 |
| 7,041,127 | B2 | 5/2006 | Ledergerber |
| 2003/0125797 | A1 | 7/2003 | Chobotov et al. |
| 2007/0043432 | A1* | 2/2007 | Perouse ............... 623/1.36 |
| 2008/0178459 | A1 | 7/2008 | Barr et al. |
| 2008/0319552 | A1* | 12/2008 | Styrc ............... 623/23.7 |
| 2009/0048664 | A1 | 2/2009 | Cage |
| 2009/0088771 | A1 | 4/2009 | Nimgaard |
| 2009/0125096 | A1* | 5/2009 | Chu ............... A61F 2/07 623/1.14 |

FOREIGN PATENT DOCUMENTS

| | | | |
|---|---|---|---|
| EP | PCT/US2010/030236 | | 6/2010 |
| FR | 2865926 | A1 | 8/2005 |
| WO | WO 98/19631 | | 5/1998 |
| WO | 0027310 | A2 | 5/2000 |
| WO | 0106952 | A1 | 2/2001 |
| WO | 02100473 | A1 | 12/2002 |
| WO | WO 2004/032800 | A1 | 4/2004 |
| WO | 2006026377 | A1 | 3/2006 |
| WO | WO 2009/064671 | A1 | 5/2009 |

OTHER PUBLICATIONS

Examination Report for EP 10714405.7 dated Jun. 17, 2014, 4 pages.
International Preliminary Report on Patentability for PCT/US2010/030236 dated Oct. 11, 2011, 6 pages.
International Search Report and Written Opinion for PCT/US2010/030236 dated Jun. 29, 2010, 12 pages.
Combined Search and Examination Report for GB0906062.5 dated Aug. 7, 2009, 3 pages.

* cited by examiner

INTRODUCER ASSEMBLY AND IMPLANTABLE MEDICAL DEVICE

TECHNICAL FIELD

The present invention relates to an introducer assembly, an outer sheath for an introducer assembly and to an implantable medical device such as, but not limited to, a stent or stent graft.

BACKGROUND OF THE INVENTION

The use of stents, stent grafts, occluders, filters and other implantable medical devices introduced endoluminally for treating a damaged or diseased area of a patient is well known. With many such devices it is necessary to fix the device within a lumen of a patient in such a manner that it can be assured that the implantable medical device will remain in position throughout its period of use, in some cases substantially indefinitely. It is also important to be able to fix the device in position while this is being deployed, typically by being expanded from a contracted configuration for insertion into a patient. For this purpose, it is well known to provide barbs on such devices. These are typically pin-like projections fitted to the implantable medical device, which projections in use extend outwardly of the device so as to penetrate the walls of the lumen in which the device is to be fitted, thereby acting as anchors for anchoring the device in position.

Barbs of this nature can take a variety of forms and have a variety of characteristics in dependence upon the particular requirements for a medical device or medical application. In many instances, the barbs are fixed to a support structure of the implantable medical device, such as a stent. These may be fixed so as to be integral with the support structure, such fixing being provided, for example, by welding a barb to the support structure or by any other suitable fixing. The barbs may be flexible and thus able to be trained to a compressed configuration in which they remain tight against a compressed support structure while on the introducer and able to expand to an operative position extending beyond the perimeter of the support structure of the medical device during deployment. In some instances the barbs or at least a part of the barbs may be substantially rigid.

For the purposes of delivering such a medical device within a patient, it is important to be able to deliver the medical device, with its barbs, endoluminally within a patient, in which case the medical device is typically deliverable by means of a relatively small diameter and flexible introducer. This generally results in the barbs needing to be flexible enough so that they can be pushed against an inner carrier element of the introducer and held in that position by an outer sheath or other holding device to retain the barbs compressed. This invariably places certain limits upon the structure and design of such barbs.

U.S. Pat. No. 5,755,777 discloses an expandable transluminal graft prosthesis for repair of an aneurism which is provided with a plurality of barb elements at the proximal and distal ends of the graft, fixed to internal surfaces of end stents provided at these ends of the prosthesis. When located on an introducer, the end stents act to push the barbs attached thereto inwardly towards a carrier cannula such that the barbs are held spaced from an outer sheath which covers the prosthesis up to the point at which it is to be deployed within a patient.

DISCLOSURE OF THE INVENTION

It has been realised that in some applications it would be advantageous to provide one or more relatively stiff barbs on a medical prosthesis. Such barbs would be advantageous in situations in which the prosthesis is liable to move within a lumen of a patient, for example as a result of a particular location of that prosthesis with respect to strength of fluid flow and/or the particular nature of the lumen. For such example applications, it is considered that it would be advantageous to provide barbs which are substantially inflexible and thus therefore relatively stiff, as these provide much stronger anchoring compared to the anchoring which could be provided by flexible barbs.

In other instances, it has been considered advantageous to provide relatively short barbs, for example in cases where it is not desired or otherwise disadvantageous to have barbs which could penetrate relatively deeply within the walls of a patient's lumen or other organ. For this purpose, it can be particularly advantageous to have short and stiff barbs.

Such barb structures, however, present difficulties during deployment of the medical prosthesis as they cannot be readily compressed within the introducer. This has generally meant that they have been unsuitable.

The present invention seeks to provide an improved introducer for the deployment of implantable medical devices, an improved sheath structure for such introducers and to an improved implantable medical device.

According to an aspect of the present invention, there is provided an introducer assembly for introducing an implantable medical device within a patient, which introducer assembly is provided with an outer sheath operable to cover an implantable medical device carried on the introducer until deployment, which outer sheath includes an inner wall, wherein the inner wall includes one or more channels extending in a longitudinal direction of the sheath.

The channel or channels, in practice, extend to a distal end of the sheath. They provide a space for accommodating, in the preferred embodiment, the substantially non-compressible barbs of an implantable medical device, such that the device can be carried on and deployed from the introducer without the barbs snagging or otherwise catching on the components of the introducer, in particular the sheath.

Advantageously, the channel or channels extend along the internal wall of the sheath for a distance at least equivalent to the length of the implantable medical device to be carried on the introducer. This enables the implantable medical device to be provided with a corresponding number of barbs at any desired position along the length of the implantable medical device.

In the preferred embodiment, the internal wall of the sheath provides one or more projections extending towards a radial centre point of the sheath. The projection or projections are operable to provide a compressing force for compressing an implantable medical device towards the radial centre point of the sheath and in practice towards a supporting cannula or other element of the introducer.

Advantageously, the projection or projections are in the form of a rib extending in a longitudinal direction of the sheath.

In the preferred embodiment, there are provided at least two projections, spaced from one another in a radial direction of the sheath, wherein the space between the projections provides a channel.

In use, the channel between the projections is able to accommodate a non-compressible element of an implantable medical device with the projections compressing those parts of the implantable medical device either side of the non-compressible element towards the centre point of the sheath and thus onto the carrier cannula or other element.

In the preferred embodiment there is provided a plurality of channels within the internal wall of the sheath. Advantageously, these channels are substantially evenly spaced in a radial direction around the inner wall of the sheath.

The channels are preferably of a limited length, extending from a distal end of the sheath, with a major portion of the sheath having a substantially smooth internal wall.

It is envisaged that the sheath would typically be substantially round in transverse cross-section. In the preferred embodiment, thus, the sheath and internal support for supporting the implantable medical device, which would be of similar round cross-section to the sheath, can assure that the introducer retains a substantially even flexibility in all radial directions in order to optimise trackability and pushability of the introducer within a patient.

It is not excluded that the channels and/or ribs could extend for substantially the entire length of the sheath. This would enable the sheath to be extruded or otherwise formed with the channels and/or ribs in a single manufacturing operation.

According to another aspect of the present invention, there is provided a sheath for an introducer assembly operable to cover an implantable medical device carried on the introducer until deployment, which sheath includes an inner wall, wherein the inner wall includes one or more channels extending in a longitudinal direction of the sheath.

According to another aspect of the present invention, there is provided an implantable medical device with at least one substantially non-compressible barb.

Preferably, the implantable medical device includes a support structure, the barb being integral with the support structure. The support structure may be a stent. The barb may be a cut or cast portion of the structure.

Advantageously, the implantable medical device is a stent or stent graft provided with a plurality of barbs, said barbs extending radially outwardly from a periphery of the stent or stents forming the stent or stent graft. The device could equally be any other type of implantable medical device, including a vena cava filter, an occluder or any other implantable medical device or prosthesis.

According to another aspect of the present invention, there is provided a stent or stent ring provided with at least one substantially non-compressible barb. Preferably, the at least one barb is integral with the stent ring.

BRIEF DESCRIPTION OF THE DRAWING

Embodiments of the present invention are described below, by way of example only, with reference to the accompanying drawings, in which.

BEST MODE FOR CARRYING OUT THE INVENTION

Figure 1:
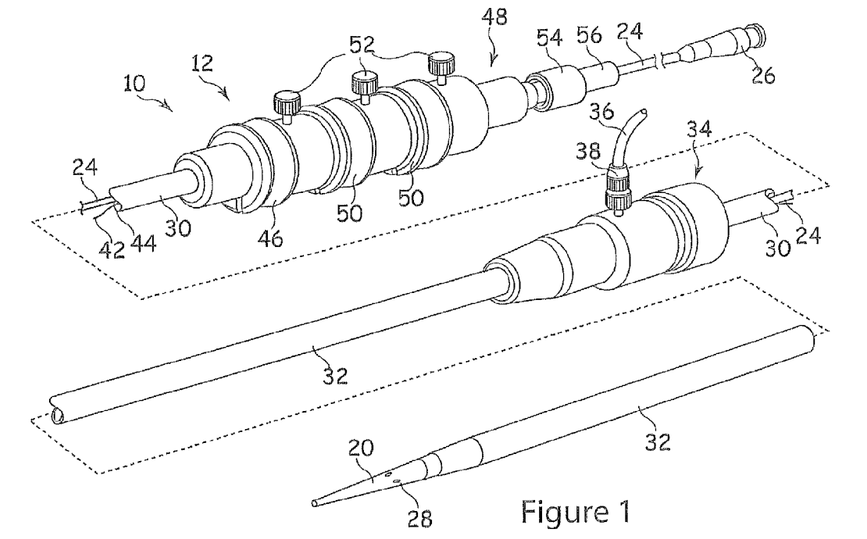
FIGS. 1 and 2 show an embodiment of a known deployment device.
Figure 2:
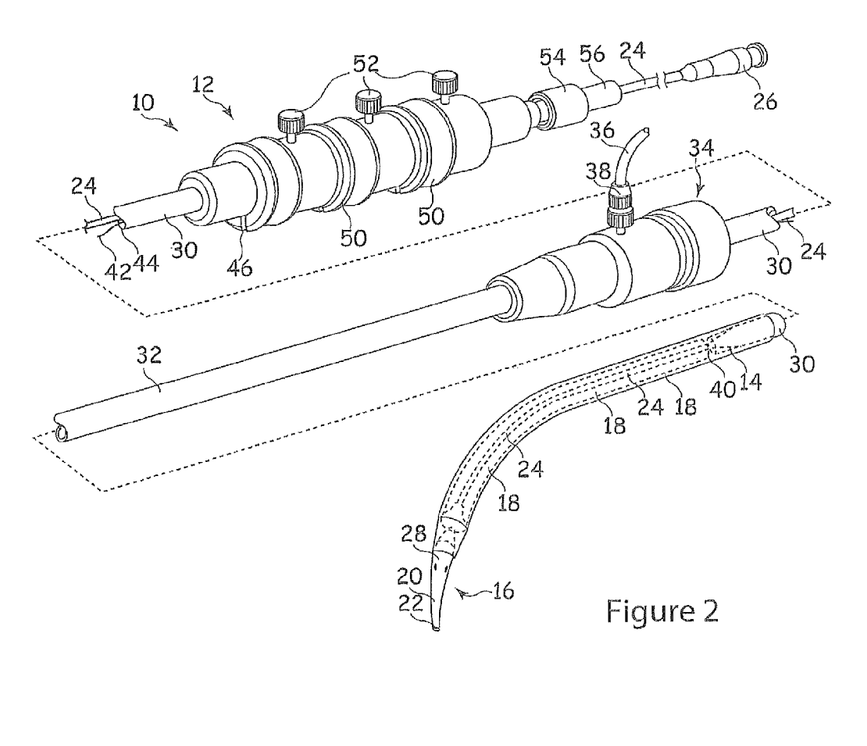

Referring to FIGS. 1 and 2, the introducer 10 includes an external manipulation section 12, a distal attachment region 14 and a proximal attachment region 16. The distal attachment region 14 and the proximal attachment region 16 secure the distal and proximal ends of the implant 18, respectively. During the medical procedure to deploy the implant 18, the distal and proximal attachment regions 14 and 16 will travel through the patient's lumen to a desired deployment site. The external manipulation section 12, which is acted upon by a surgeon to manipulate the introducer, remains outside of the patient throughout the procedure.

The proximal attachment region 16 of the introducer 10 includes a dilator tip 20, which is typically provided with a bore 22 therein for receiving a guide wire (not shown) of conventional type. The longitudinal bore 22 also provides a channel for the introduction of medical reagents. For example, it may be desirable to supply a contrast agent to allow angiography to be performed during placement and deployment phases of the medical procedure.

A guide wire catheter 24, conventionally made from a flexible thin walled metal tube, is fastened to the dilator tip 20. The guide wire catheter 24 is flexible so that the introducer 10 can be advanced along a relatively tortuous vessel, such as a femoral artery, and so that the distal attachment region 14 can be longitudinally and rotationally manipulated. The guide wire catheter 24 extends through the introducer 10 to the manipulation section 12, terminating at a connection device 26, in conventional manner.

The connection device 26 is designed to accept a syringe to facilitate the introduction of reagents into the inner catheter 24. The guide wire catheter 24 is in fluid communication with apertures 28 in the flexible dilator tip 20. Therefore, reagents introduced into connection device 26 will flow to and emanate from the apertures 28.

A pusher sheath or rod 30 (hereinafter referred to as a pusher member), typically made from a plastics material, is mounted coaxial with and radially outside of the guide wire catheter 24. The pusher member 30 is "thick walled", that is the thickness of its wall is preferably several times greater than that of the guide wire catheter 24.

A sheath 32 extends coaxially over and radially outside of the pusher member 30. The pusher member 30 and the sheath 32 extend distally to the manipulation region 12.

The implant 18, which may be a stent, a stent-graft or any other implant or prosthesis deliverable by this device 10, is retained in a compressed condition by the sheath 32. The sheath 32 extends distally to a sheath manipulator and haemostatic sealing unit 34 of the external manipulation section 12. The haemostatic sealing unit 34 includes a haemostatic seal (not shown) and a side tube 36 held to the unit 34 by a conventional luer lock 38.

The sheath manipulator and haemostatic sealing unit 34 also includes a clamping collar (not shown) that clamps the sheath 32 to the haemostatic seal and a silicone seal ring (not shown) that forms a haemostatic seal around the pusher rod 30. The side tube 38 facilitates the introduction of medical fluids between the pusher rod 30 and the sheath 32. Saline solution is typically used.

During assembly of the introducer 10, the sheath 32 is advanced over the proximal end of the dilator tip 20 of the proximal attachment region 16 while the implant 18 is held in a compressed state by an external force. A suitable distal attachment (retention) section (not visible in this view) is coupled to the pusher rod 30 and retains a distal end 40 of the prosthesis 18 during the procedure. The distal end of the prosthesis 18 is provided with a loop (not shown) through which a distal trigger wire 42 extends. The distal wire also extends through an aperture (not shown in FIGS. 1 and 2) in the distal attachment section 40 into an annular region 44 between the inner catheter 24 and the pusher rod 30. The distal trigger wire 42 extends through the annular space 44 to the manipulation region 12 and exits the annular space 44 at a distal wire release mechanism 46.

A proximal portion of the external manipulation section 12 includes at least one release wire actuation section 50 mounted on a body 48, in turn mounted onto the pusher member 30. The guide wire catheter 24 passes through the body 48. The distal wire release mechanism 46 and the proximal wire release mechanism 50 are mounted for slidable movement on the body 48.

The positioning of the proximal and distal wire release mechanisms 46 and 50 is such that the proximal wire release mechanism 46 must be moved before the distal wire release mechanism or mechanisms 50 can be moved. Therefore, the distal end of the implant 18 cannot be released until a self-expanding zigzag stent thereof has been released. Clamping screws 52 prevent inadvertent early release of the prosthesis 18. A haemostatic seal (not shown) is included so that the release wires can extend out through the body 48 without unnecessary blood loss during the medical procedure.

A proximal portion of the external manipulation section 12 includes a pin vise 54 mounted onto the proximal end of the body 48. The pin vise 54 has a screw cap 56. When screwed in, vise jaws (not shown) of the pin vise 54 clamp against or engage the guide wire catheter 24. When the vise jaws are engaged, the guide wire catheter 24 can only move with the body 48 and hence it can only move with the pusher member 30. With the screw cap 56 tightened, the entire assembly can be moved together as one piece.

Once the introducer assembly 12 is in the desired deployment position, the sheath 32 is withdrawn to just proximal of the distal attachment section 14. This action releases the middle portion of the implant 18, in this example a stent or stent-graft, so that it can expand radially. Consequently, the stent or stent-graft 18 can still be rotated or lengthened or shortened for accurate positioning. The proximal end self-expanding stent however, is still retained at the dilator tip 16 by means of the release wires. Also, the distal end of the stent or stent-graft 18 will still retained within the sheath 32.

Next, the pin vise 54 is released to allow small movements of the guide wire catheter 24 with respect to the pusher rod 30 to allow the stent or stent-graft 18 to be lengthened, shortened, rotated or compressed for accurate placement in the desired location within the lumen. X-ray opaque markers (not shown) may be placed along the stent or stent-graft 18 to assist with placement of the prosthesis.

When the proximal end of the stent or stent-graft 18 is in place, the proximal trigger wire is withdrawn by distal movement of the proximal wire release mechanism. The proximal wire release mechanism 50 and the is proximal trigger wire can be completely removed by passing the proximal wire release mechanism 50 over the pin vise 54, the screw cap 56 and the connection unit 26.

Next, the screw cap 56 of the pin vise 54 is loosened, after which the inner catheter 24 can be pushed in a proximal direction to move the dilator tip 20 in a proximal direction. When the dilator tip 20 no longer surrounds the end of the stent or stent-graft 18, it expands to engage the lumen walls of the patient. From this stage on, the proximal end of the stent or stent-graft 18 cannot be moved again.

Once the proximal end of the stent or stent-graft 18 is anchored, the sheath 32 is withdrawn distally of the distal attachment section 14, which withdrawal allows the distal end of the stent or stent-graft 18 to expand. At this point, the distal end of the stent or stent-graft 18 may still be repositioned as needed.

Figure 3:
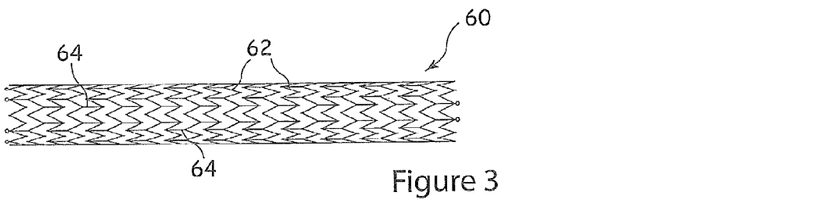
FIG. 3 shows an example of a stent.

Referring now to FIG. 3, there is shown an example of stent which could be constructed to incorporate the teachings disclosed herein. FIG. 3 is an example of the applicant's Zilver™ stent. This is a stent of unitary construction made of Nitinol and is of self-expanding form. The stent could, however, be made of any other material, including balloon expandable materials and could have other structures. As will be apparent in FIG. 3, the stent 60 is formed of a plurality of stent rings 62 which are coupled to one another by a plurality of tie bars 64. Such a structure of stent is well known in the art.

Figure 4:
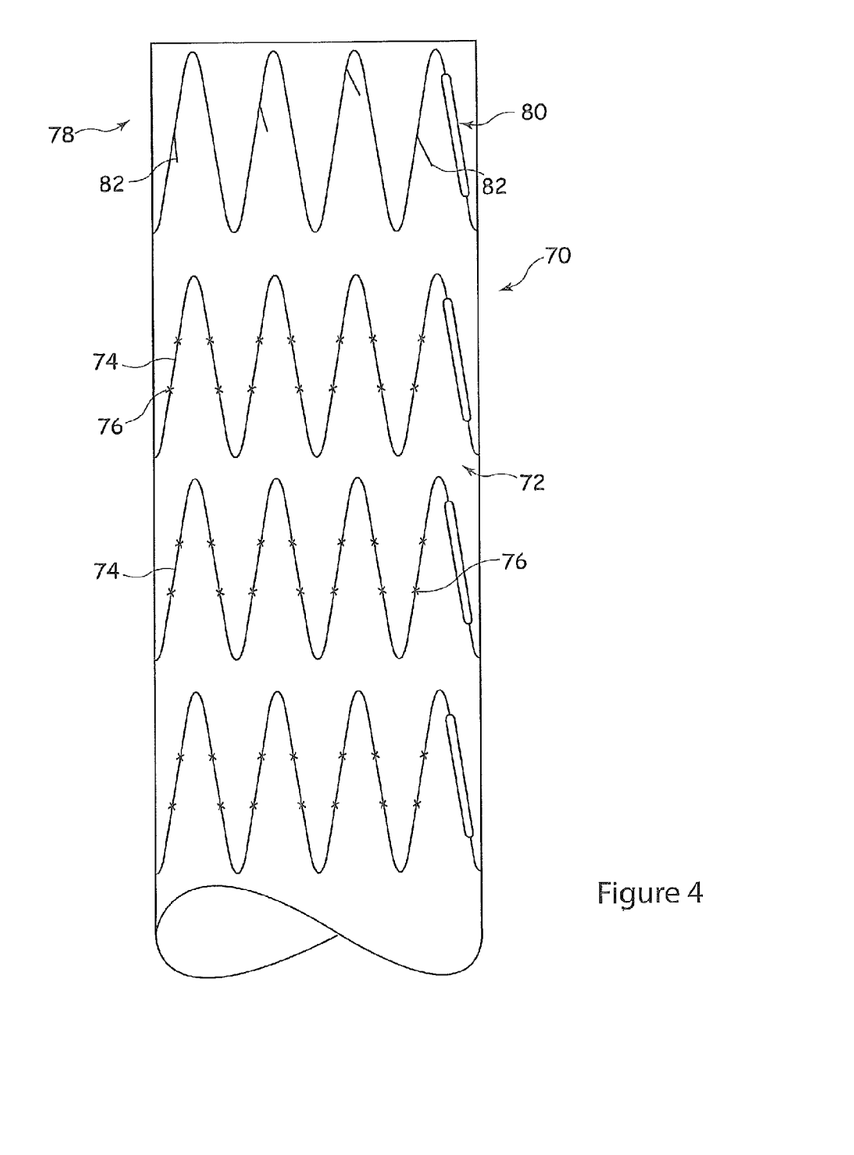
FIG. 4 shows in schematic form an example of stent graft.

Referring now to FIG. 4, there is shown an example of stent graft assembly 70, which is formed of a tube 72 of graft material to which there are attached a plurality of stent rings 74. These are attached by, for example, suturing and FIG. 4 shows a plurality of sutures 76 fixing the stents 74 to the graft tube 72.

At the proximal end 78 of the stent graft 70 there is provided an end stent 80 which in this example is positioned within the extremity of the graft tube 70 but may typically extend beyond that so as to constitute a bare stent is of a type well known in the art. The stent 80 is provided with a plurality of barbs 82 which in use extend beyond the radial periphery of the graft material 70 and the stents 74, 80. These barbs 82 have the function of anchoring the stent graft 70 to the internal walls of a patient's lumen. Barbs are well known in the art. As explained above, they are typically a set of components which are attached to a stent or graft tubing and are typically of flexible construction.

Although the example of stent shown in FIG. 3 does not have any barbs shown, the stent is of such a type that it could be provided with barbs similar to the barbs 82. These barbs could be provided at a proximal end of the stent (as with the stent graft 70) as well as/or at other positions along the stent or stent graft. The same applies in the case of other medical devices.

Figure 5:
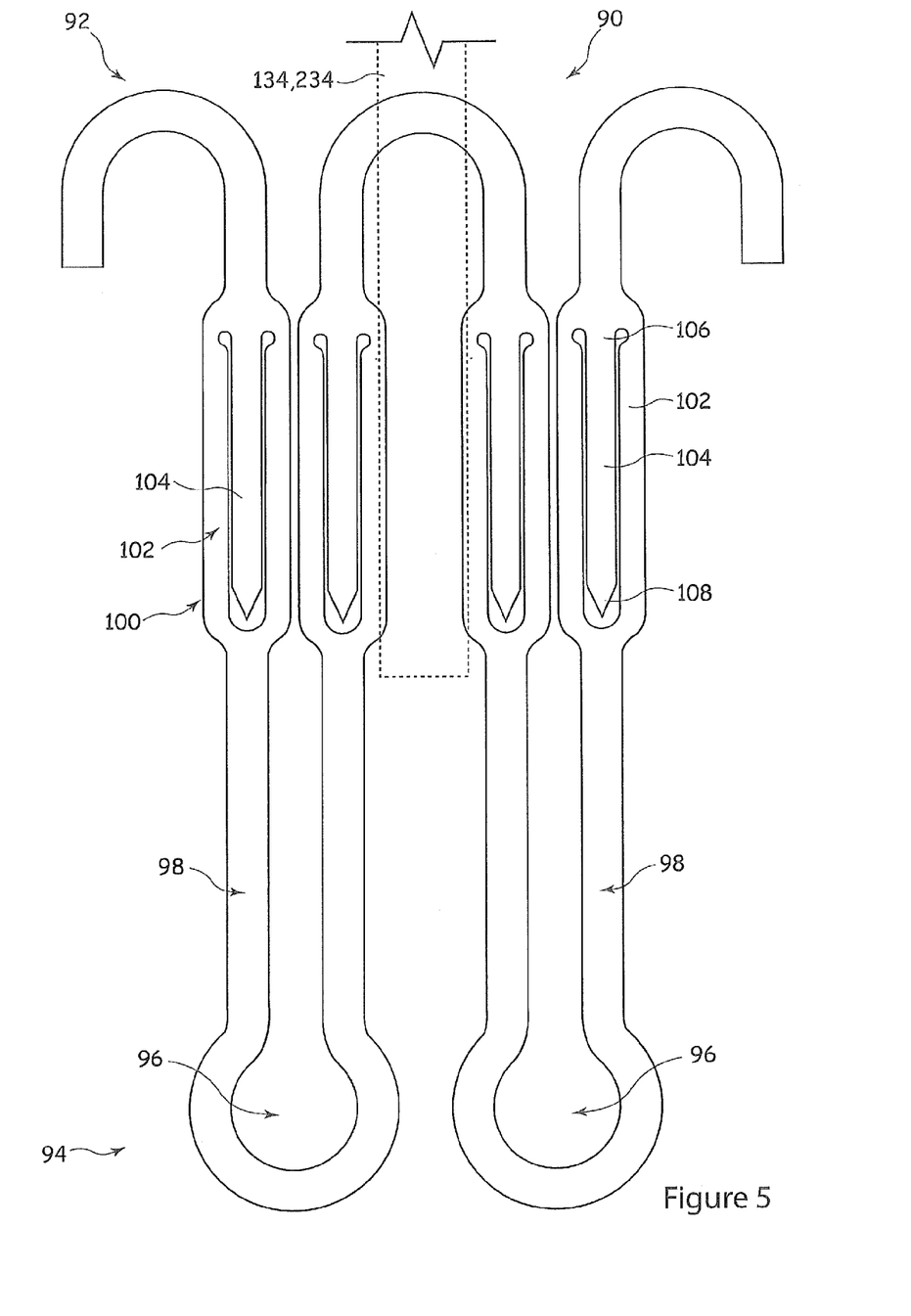
FIG. 5 shows a portion of an end stent for a stent of FIG. 3 or stent graft of FIG. 4 or other implantable medical device.

Referring now to FIG. 5, there is shown an embodiment of stent ring 90 for use as an end-most stent of a stent or stent graft but could equally be used in other implantable medical devices. The stent 90 is shown in a compressed configuration.

The stent 90, of which only a part of the stent ring is shown in FIG. 5, includes a proximal end 92 and a distal end 94. This particular design of stent ring 90 is intended to be fitted as a bare stent at the end of a graft tube similar to the graft tube 70 of the example of stent graft shown in FIG. 4. For this purpose, the distal end 94 of the stent ring 90 is provided with a plurality of looped ends 96 through which suture thread can be sewn in order to tie the ends 94 to the graft tubing 70. The remainder of the stent 90, and in particular the ends 92, can extend beyond the extremity of the graft tubing 70 so as to constitute a bare stent. This is not necessarily the case as the entirety of the stent ring 90 could be located within the extent of the graft tubing to which it is attached and can be located either on the inside of the graft tubing or on the outside.

Typically, the stent ring 90 would be cast or laser cut into the form shown in FIG. 5.

As can be seen in FIG. 5, the struts 98 forming the stent ring 90 and extending between the proximal and distal ends 92, 94 of the stent have at intermediate positions thereof a barb structure 100. This is formed, in this example, as an enlarged zone of the stent strut 98 with what could be described as a framework 102 lying either side of a barb 104.

The barb 104 has a first end 106 which is connected to and integral with the stent strut 98 and a free end 108 which is cut or otherwise formed into a sharp, pointed, end. The barb 104 extends out of the plane of the stent struts 98 and of the envelope elements 102 either side of the barbs 104, by being bent at the end 106 or by being generally curved from the end 106 to the pointed end 108.

In this example, the barbs 104 would extend out of the plane of the paper in the view of FIG. 5 and in practice to the outside of the radial periphery of the stent 90.

The envelope elements 102 provide a unitary integral structure for the struts 98. Although in this embodiment two envelope elements 102 are provided, other embodiments could have a single element 102 which connects to the remainder of the strut 98 or otherwise forms an integral part of the strut 98, with the barb 104 extending to one side of the element 102. Any particular structural arrangement could be provided in dependence upon the structure of the stent or other medical device and its intended medical application.

In this embodiment, the barbs 104 are substantially rigid in order to provide strong and effective anchoring functions. By substantially rigid it is meant that the barbs 104 will not deflect to any significant degree, or only minimally, during use of the stent graft or other implantable medical device and it is preferred that the barbs 104 will substantially retain their configuration both during storage of the medical device on the introducer, during deployment of the medical device and once the medical device is in situ in a patient. In other words, they would always extend outwardly of the radial periphery of the major portion of the medical device.

The skilled person will appreciate that the particular design of stent 90 shown in FIG. 5 is intended to be an end stent positioned at the proximal end of a sent graft or other medical device, that is at the end closest to the heart and what could be described as the upstream end of the medical device. Similar stents to the stent 90 could be designed for other locations within a stent graft or other medical device, such as at its distal end and/or at any position intermediate the proximal and distal ends of the medical device. In such a case, the ends 92, 94 of the stent 90 could have slightly different configurations in dependence upon the positioning of the stent within the medical device and whether or not the stent is to be a bare stent or located entirely within the zone of the graft material or other covering. It would be appreciated also that in the case where the stent 90 is not intended to be a bare stent, the proximal ends 92 of the stent could have a similar structure to the ends 94.

As the barbs 104 of the stent 90 are designed to be substantially rigid and to retain their extended position beyond the radial perimeter of the stent 90 both when the latter is the point condition and when it is compressed onto an introducer, the barbs 104 present difficulties in the placement of the medical device on an introducer, as a result of the risk of these snagging on the internal wall of the introducer sheath and preventing proper deployment of the medical device.

In FIG. 5 the barbs 104 are shown extending in what could be described as a proximal direction, that is in a downstream blood flow direction when the medical device is in situ in a patient. It is also envisaged that the barbs 104 could point in the opposite direction to that shown, that is in a distal or upstream direction. This alternative may be preferable in some medical applications and may also be advantageous at the distal end of the medical device. In the view of FIG. 5, such barbs would point upwardly.

The stent 90 need not be a bare stent but could be located entirely or substantially entirely on or in a graft element.

Figure 6:
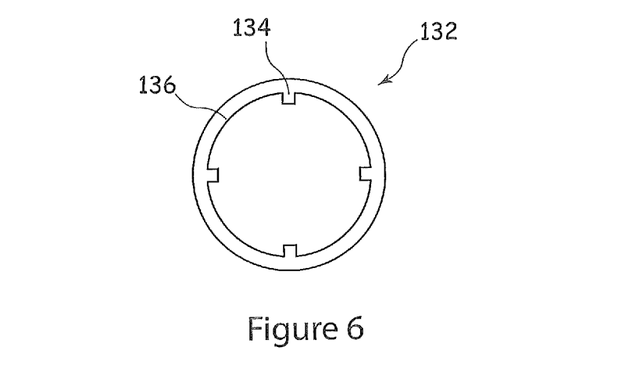
FIG. 6 is a transverse cross-sectional view of an embodiment of sheath.

Referring now to FIG. 6, there is shown a transverse cross-sectional view of an embodiment of sheath 132 which can be used in place of a conventional sheath used in existing introducer assemblies. The sheath 132 has an overall structure equivalent to the sheath 32 shown in the introducer of FIGS. 1 and 2, having an outer external diameter which is substantially circular in axial cross-section. It thus has the flexibility and trackability characteristics of known introducer system sheaths and can be formed of the same or similar materials. The sheath 132 differs from conventional sheaths by way of its internal configuration. In the embodiment of FIG. 6, the sheath 132 is provided with a plurality of ribs 134 of substantially rectangular axial cross-section and which extend longitudinally along the sheath from the distal end of the sheath (which in practice abuts and overlies the dilator tip 16). Between these ribs 134 there are provided a plurality of channels 136, these channels 136 being in effect recessed relative to the radial spacing between the ribs 134 and the centre-point of the sheath 132. The embodiment of FIG. 7 is similar to the embodiment of FIG. 6 although it is provided with more ribs 234 and thus provides more longitudinal channels 136.

Figure 7:
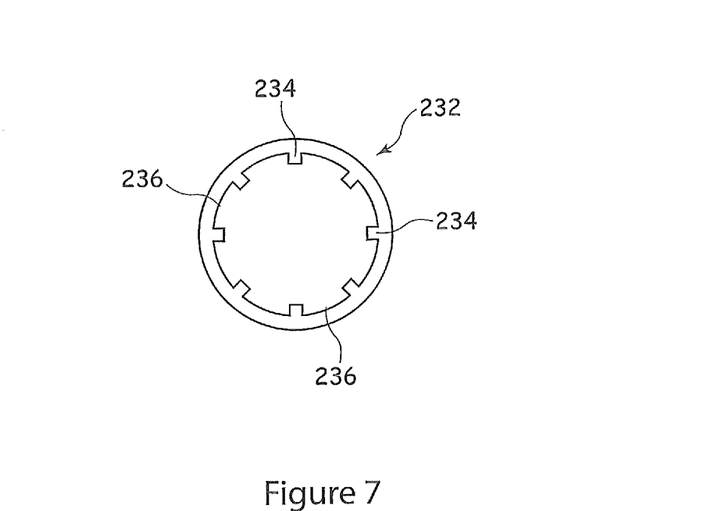
FIG. 7 is a transverse cross-sectional view of another embodiment of sheath.

In both embodiments of FIGS. 6 and 7, the ribs 134 and 234, and thus the channels 136 and 236, may extend only part-way along the sheath 132, although in other embodiments they could extend along the entirety of the length of the sheath 132 or for a substantial part of this. By substantial part it is intended to mean a length of ribs and channels which exceeds the length of an implantable medical device which would be carried by the introducer assembly.

In the case where the ribs and channels extend part-way along the internal walls of the sheath 132, 232, these are preferably of a length at least as long as the medical device carried on the introducer. However, in some circumstances, for example where it is known that the barbs are located at only some positions of the medical device, such as at its proximal end, the ribs and channels can extend only to the position of these barbs or at least substantially to overlie the position of the rear-most barbs, when the device is mounted on the introducer.

An arrangement whereby the ribs and channels extend the whole length of the sheath 132, 232 can be made in a simple and single manufacturing process, such as by extrusion. On the other hand, it can be advantageous to retain at least some portion of the sheath 132, 232 with a substantially circular internal wall for internal sealing purposes. In the case of channels which extend only part-way along the inside of the sheath 132, 232, these could be formed by machining or other suitable manufacturing process.

The number of ribs and channels on the inside of the sheath 132, 232 would in practice be dependent upon the particular design of the stent and number and position of the barbs. Referring again to FIG. 5, there is shown in dotted outline a possible arrangement for one of the ribs 134, 234. It would be appreciated that other ribs 134, 234 would also be arranged circumferentially around the stent 90 in similar manner to the rib shown in dotted outline of FIG. 5.

As can be seen in FIG. 5, the rib 134, 234 extends over a part of the stent 90, in this particular example over two facing enveloping elements 102 of the stent 90. This is only one example and suitable in this particular instance if the barbs 104 are the only and rear-most barbs of the medical device.

In practice, the rib 134, 234 will assist in pushing the stent 90 and, as appropriate, the enveloping elements 102, towards the carrier cannula 24 of the introducer and thus to compress the stent 90 onto the carrier element. The channels 136, 236 are located either side of the rib 134, 234 and in practice such that the barbs 104 can extend into the channels 136, 236 with sufficient radial space that the stent 90 can be held within the sheath 132, 232 without the barbs 134 coming into contact with any part of the sheath wall and therefore without risk of barbs snagging against the internal surfaces of the sheath 132, 232.

More specifically, when the sheath 132, 232 is withdrawn with respect to the internal assemblies of the introducer and thus of the implantable medical device carried on the introducer, the ribs will slide alongside the barbs 104, retaining the barbs 104 within the channels 136, 236 and thus will ensure that the barbs 104 at no stage snag against the internal walls of the sheath 132, 232. It is only once the barbs 104 have moved completely out of the sheath 132, 232, that is passed beyond the ends of the channels 136, 236, that the stent 90 and thus the barbs 104 will be able to expand radially outwardly (unless otherwise secured to the introducer by some other securing element of the type known in the art) and upon such expansion to engage into the inner walls of the vessel into which the medical device is to be deployed. Thus, stiff barbs can be provided on such a device for risking any disadvantages of deployment of a medical device carrying such barbs.

This arrangement of ribs, channels and barbs can ensure that the medical device carried in the introducer remains aligned with the sheath 132, 232 during deployment, thus facilitating the correct orientation of the medical device during the deployment procedure. In some prior art systems it is possible for the medical device to rotate within the introducer and thus for the orientation of the medical device within the introducer not to match the orientation of the outer sheath during the deployment operation. This can occur when the introducer is passed through particularly tortuous vessels in a patient.

It is preferred that the channels 136, 236 are recessed with respect to the entirety of the other internal surfaces of the sheath 132, 232, that is that the channels form the deepest part of the internal walls of these sheaths. On the other hand, in other embodiments, any sections of the sheath 132, 232 not provided with the ribs 134, 234 could have an internal wall coterminous and thus aligned with the channels 136, 236, in which case the ribs 134, 234 represent protrusions extending internally relative to the remainder of the internal surface of the sheath 132, 232 towards the centre line of the sheath. This has the advantage of minimising the thickness of the wall of the sheath 132, 232 in order to increase the flexibility and thus the trackability of the introducer while still retaining sufficient wall thickness at the zones of the channels 136, 236. The ultimate choice as to whether the channels are recessed with respect to the remainder of the internal surfaces of the sheath or whether the ribs represent protrusions with respect to the remainder of the inner walls will be dependent upon the particular type of introducer, its size, the medical application to which it is intended to be used and designer preference.

While the embodiments of FIGS. 6 and 7 show rib/channel arrangements of substantially even widths, there could be provided ribs/channels or different widths around the internal circumference of the sheath.

What is claimed is:

1. An introducer assembly including an introducer and an implantable medical device comprising a stent carried in the introducer and including a single plurality of non-compressible barbs each having a free end that extends radially outwardly of the medical device, which introducer is provided with an outer sheath operable to cover the implantable medical device until deployment, the outer sheath including an inner wall provided with one or more channels extending in a longitudinal direction of the sheath, such that each non-compressible barb is located in the or a respective channel of the sheath, and one or more projections extending towards a radial center-point of the sheath for compressing the implantable medical device towards the radial center-point such that each barb can extend into the channel without contacting the inner wall of the sheath, wherein each barb maintains its shape and position relative to the stent upon expansion, wherein the medical device comprises struts having an inner surface and an outer surface and each barb extends only from the outer surface of a strut with no part of the barb extending from the inner surface of a strut, wherein each of the struts from which a barb extends further includes a framework disposed about the barb, wherein the stent has a radial periphery in a compressed configuration within the sheath and in the compressed configuration, the barbs extend outside the radial periphery of the stent and out of the plane of the struts and the framework, wherein the barbs retain their configuration both during storage of the medical device on the introducer, during deployment of the medical device and once the medical device is in situ in a patient, and wherein each barb is integral with and formed out of the strut.

2. An introducer assembly according to claim 1, wherein the channel or channels extend to a distal end of the sheath.

3. An introducer assembly according to claim 1, wherein the channel or channels extend along the internal wall of the sheath for a distance at least equivalent to the length of the implantable medical device.

4. An introducer assembly according to claim 1, wherein the projection or projections are in the form of one or more ribs extending in a longitudinal direction of the sheath.

5. An introducer assembly according to claim 1, wherein there are provided at least two projections, spaced from one another in a radial direction of the sheath, wherein the space between the projections provides a channel.

6. An introducer assembly according to claim 1, wherein there is provided a plurality of channels within the internal wall of the sheath and wherein the channels are substantially evenly spaced in a radial direction around the inner wall of the sheath.

7. An introducer assembly according to claim 1, wherein a major portion of the sheath has a substantially smooth internal wall.

8. An introducer assembly according to claim 1, wherein the sheath is substantially round in transverse cross-section.

* * * * *

UNITED STATES PATENT AND TRADEMARK OFFICE
CERTIFICATE OF CORRECTION

PATENT NO.       : 9,724,220 B2                                          Page 1 of 1
APPLICATION NO. : 12/755880
DATED            : August 8, 2017
INVENTOR(S)      : Erik Edelboe Rasmussen It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 512 days.

Signed and Sealed this
Twenty-fifth Day of September, 2018

Andrei Iancu
*Director of the United States Patent and Trademark Office*